(12) United States Patent
Hefner et al.

(10) Patent No.: US 8,540,936 B2
(45) Date of Patent: Sep. 24, 2013

(54) TURBINE BLADE EROSION SENSOR

(75) Inventors: Rebecca Evelyn Hefner, Simpsonville, SC (US); Paul Stephen DiMascio, Greer, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/253,582

(22) Filed: Oct. 5, 2011

(65) Prior Publication Data

US 2013/0089463 A1   Apr. 11, 2013

(51) Int. Cl.
| | |
|---|---|
| *G01N 17/00* | (2006.01) |
| *G01R 27/08* | (2006.01) |
| *C03C 27/00* | (2006.01) |
| *C03C 29/00* | (2006.01) |
| *B63H 1/26* | (2006.01) |
| *B63H 7/02* | (2006.01) |
| *B64C 11/16* | (2006.01) |
| *B64C 27/46* | (2006.01) |

(52) U.S. Cl.
USPC ............. 422/53; 138/104; 324/700; 428/632; 416/224

(58) Field of Classification Search
USPC ................... 422/53; 436/6; 73/86; 324/700
See application file for complete search history.

(56) References Cited

U.S. PATENT DOCUMENTS

| | | | |
|---|---|---|---|
| 3,015,950 A | 1/1962 | Doctor et al. | |
| 4,768,373 A | 9/1988 | Spencer | |
| 5,228,478 A * | 7/1993 | Kleisle | 138/104 |
| 6,946,855 B1 * | 9/2005 | Hemblade | 324/700 |
| 7,270,890 B2 * | 9/2007 | Sabol et al. | 428/632 |
| 2008/0159870 A1 * | 7/2008 | Hong | 416/224 |

* cited by examiner

*Primary Examiner* — Jill Warden
*Assistant Examiner* — Julie Tavares
(74) *Attorney, Agent, or Firm* — Dority & Manning, P.A.

(57) ABSTRACT

An erosion sensor that can separately monitor erosion and corrosion of a substrate, such as a wind turbine blade or a turbine blade used in devices such as gas turbines, aircraft engines, microturbines, steam turbines, and the like is disclosed. The sensor can include a first element or "erosion part" that is made of a corrosion resistant material. The first element of the sensor has similar erosion properties to the substrate being monitored. The sensor can further include a second element or a "corrosion part" that is made of a material having similar erosion and corrosion properties to the substrate. The sensor can provide an erosion indicator based on the erosion of the first element and a corrosion indicator based on the erosion and corrosion of the second element.

13 Claims, 5 Drawing Sheets

TURBINE BLADE EROSION SENSOR

FIELD OF THE INVENTION

The present disclosure relates generally to turbines and, more particularly to a sensor for monitoring erosion of a turbine blade.

BACKGROUND OF THE INVENTION

Wind turbine blades can suffer significantly from erosion due to exposure to the elements, such as rain, hail, sand, or other particulates. Turbine compressor blades used in devices such as gas turbines, aircraft engines, microturbines, steam turbines, and the like, suffer from erosion due to water droplets contacting the blades during operation. For instance, erosion pitting can be caused by water condensation on the blades or by water washing to remove deposits during turbine operation.

Turbine blades can also suffer from corrosion as a result of the harsh operating environment in which the turbine blades are used. Corrosion pitting works in synergy with existing erosion pits to generate an overall faster pit growth rate. Corrosion and erosion pitting can cause catastrophic failure of the turbines if left undetected or unmitigated.

It is difficult to monitor erosion and corrosion of turbine blades. For instance, wind turbine blades are typically located in remote locations and special equipment is need to access the turbine blades for inspection. Expensive machine downtime is typically required to inspect turbine compressor blades, such as blades used in gas or steam turbines, to detect and monitor erosion and corrosion pit depths.

Thus, a need exists for a sensor that can separately monitor both erosion and corrosion of a turbine blade. A sensor that can provide detection of erosion and corrosion pit depths during turbine operation, without requiring machine downtime, would be particularly useful.

BRIEF DESCRIPTION OF THE INVENTION

Aspects and advantages of the invention will be set forth in part in the following description, or may be obvious from the description, or may be learned through practice of the invention.

One exemplary embodiment of the present disclosure is directed to a sensor for monitoring erosion and corrosion of a substrate. The sensor includes a first element of corrosion resistant material having similar erosion properties to the substrate and a second element of material having similar erosion and corrosion properties to the substrate. The sensor provides an erosion indicator based at least in part on the erosion of the first element and a corrosion indicator based at least in part on the erosion and corrosion of the second element.

Another exemplary embodiment of the present disclosure is directed to an erosion sensor for monitoring erosion of a turbine blade. The erosion sensor includes at least one first element of corrosion resistant material having similar erosion properties to the turbine blade. The sensor provides an erosion indicator based at least in part on the erosion of the at least one first element.

A further exemplary embodiment of the present disclosure is directed to a system for monitoring erosion of a turbine blade. The system includes a plurality of conductive elements of corrosion resistant material having similar erosion properties to the turbine blade. The erosion sensor further includes an electrical property monitoring device configured to monitor an electrical property associated with each of the plurality of conductive elements. The electrical property monitoring device is configured to provide a signal when one of the plurality of conductive elements has been modified due to erosion. The system provides an erosion depth indicator based at least in part on the number of the plurality of conductive elements that have been modified due to erosion.

Variations and modifications can be made to these exemplary embodiments of the present disclosure.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
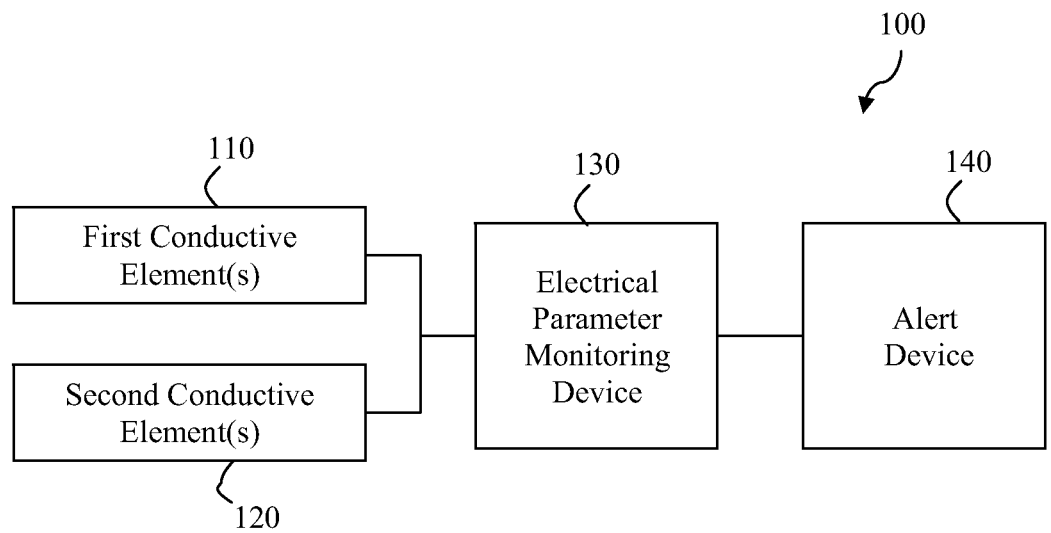
FIG. 1 depicts a block diagram of an exemplary sensor according to an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to an erosion sensor that can be configured in certain embodiments to monitor separately erosion and corrosion of a substrate, such as a wind turbine blade or a turbine blade used in devices such as gas turbines, aircraft engines, microturbines, steam turbines, and the like. The sensor can include a first element or "erosion part" that is made of a corrosion resistant material. The first element of the sensor has similar erosion properties to the substrate being monitored. The sensor provides an erosion indicator based at least in part on the erosion of the first element. As used herein, an erosion indicator is anything that can provide an indication of erosion of the substrate being monitored. For instance, an erosion indicator can be an electrical signal, a visual indicator, audible indicator, or any other indication that the substrate being monitored has suffered erosion.

The sensor can further include a second element or "corrosion part" that experiences both corrosion and erosion. The second element of the sensor preferably has similar erosion and corrosion properties to the substrate being monitored. In certain embodiments, corrosion of the substrate can be monitored by monitoring erosion and corrosion of the second element. As used herein, a corrosion indicator is anything that can provide an indication of corrosion of the substrate being monitored. For instance, a corrosion indicator can be an electrical signal, a visual indicator, audible indicator, or any other indication that the substrate being monitored has suffered corrosion.

The sensor according to exemplary embodiments of the present disclosure can provide for online monitoring of erosion and/or corrosion pit depths of a turbine blade during operation of a turbine. In this manner, the present disclosed subject matter provides for improved prediction of when mitigation measures are needed and provides for enhanced maintenance schedules and scheduling of downtime.

FIG. 1 provides a block diagram of an erosion sensor 100 according to an exemplary embodiment of the present disclosure. As illustrated, erosion sensor 100 includes a first conductive element(s) 110, a second conductive element(s) 120, an electrical parameter monitoring device 130, and an indicator device 140. As will be discussed in detail below, erosion sensor 100 can be disposed on a turbine blade or within a coating of a turbine blade to monitor erosion and/or corrosion and erosion and/or corrosion pit depth of the turbine blade.

First conductive element(s) 110 comprises a corrosion resistant material that has similar erosion properties to the substrate being monitored. As used herein, materials have similar erosion properties if the materials erode at a similar rates or if there is a known transfer function between the erosion rates of the materials. In particular embodiments, the first conductive element(s) 110 comprises a metallic foil, one or more fiber optic wires, or a conductive polymer.

The electrical parameter monitoring device 130 can be coupled to the first conductive element(s) 110 such that the electrical parameter monitoring device 130 monitors an electrical parameter associated with the first conductive element(s) 110, such as a voltage or current across the first conductive element(s). The electrical parameter monitoring device 130 detects changes in the electrical parameter associated with the first conductive element(s) 110 to determine the level of erosion of the first conductive element(s) 110 and thus the substrate.

For instance, in a particular embodiment, if the first conductive element(s) 110 becomes severed due to erosion, the first conductive element(s) 110 will no longer conduct electricity. This can be detected by an electrical parameter monitoring device 130, such as a voltage and/or current meter device, to provide an indication of erosion, including an indication of erosion pit depth, of the substrate.

In another particular embodiment, the electrical parameter monitoring device 130 detects when the first conductive element(s) 110 becomes modified due to erosion. For instance, as the cross-sectional area of the first conductive element 110 becomes reduced due to erosion, the resistance of the first conductive element(s) 110 will increase. The increase in resistance can be detected by an electrical parameter monitoring device 130, such as a voltage and/or current meter device, to provide an indication of erosion, including an indication of erosion pit depth, of the substrate.

According to certain aspects of the present disclosure, the sensor 100 can additionally include a second element(s) 120. Second conductive element(s) 120 comprises a corrosion resistant material that has similar erosion and corrosion properties to the substrate being monitored. As used herein, materials have similar erosion and corrosion properties if the materials erode and corrode at similar rates or if there is a known transfer function between the erosion and corrosion rates of the materials.

The electrical parameter monitoring device 130 can be coupled to the second conductive element(s) 120 such that the electrical parameter monitoring device 130 monitors an electrical parameter associated with the second conductive element(s) 120, such as a voltage or current across the second conductive element(s). The electrical parameter monitoring device 130 detects changes in the electrical parameter associated with the second conductive element(s) 120 to determine the level of erosion and corrosion of the first conductive element(s) 110 and thus the substrate.

Sensor 100 can further include an alert device 140. Alert device 140 can provide any suitable alert or indication associated with the erosion and/or corrosion of the substrate. For instance, the alert device 140 can provide a visual alert, audible alert, alert transmitted wirelessly to a remote device, or other suitable alert having information concerning the erosion and/or corrosion of the substrate. Those of ordinary skill in the art, using the disclosures provided herein, should understand that the present disclosure is not limited to any particular type of alert device and that any suitable alert device or type of alert can be used without deviating from the scope of the present invention.

Figure 2:
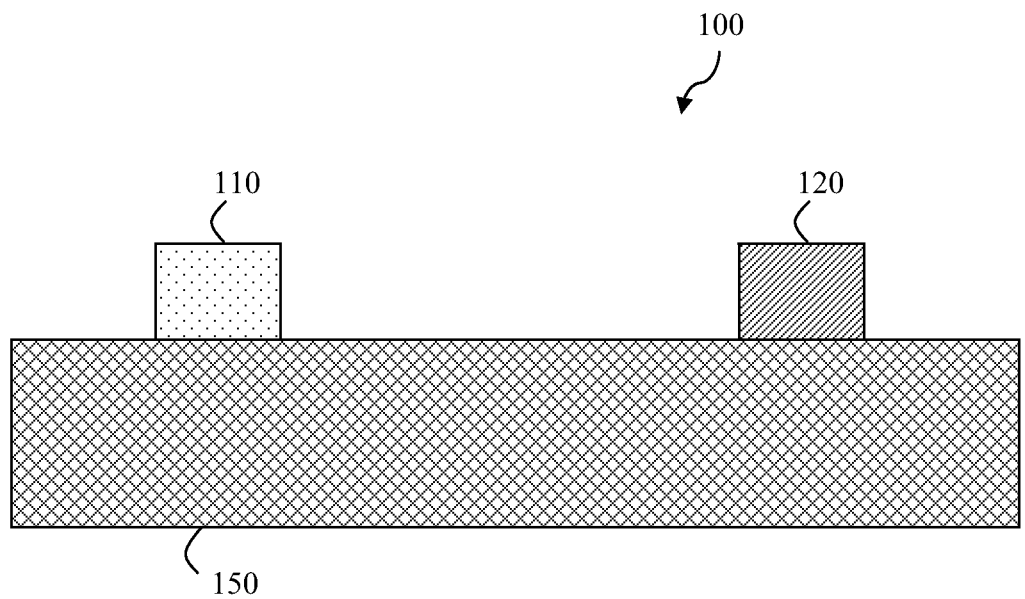
FIG. 2 depicts a sensor for monitoring erosion and corrosion disposed on a substrate according to an exemplary embodiment of the present disclosure.

FIG. 2 illustrates an exemplary sensor 100 disposed on a substrate 150 according to a particular aspect of the present disclosure. Substrate 150 can include a wind turbine blade or a turbine blade used in devices such as gas turbines, aircraft engines, microturbines, steam turbines, and the like. As shown, sensor 100 includes a planar first conductive element 110 and a planar second conductive element 120 disposed on a surface of the substrate 150. First conductive element 110 comprises a corrosion resistant material with similar erosion properties to the substrate 150. Second conductive element 120 comprises a material with similar erosion and corrosion properties to the substrate.

Figure 3:
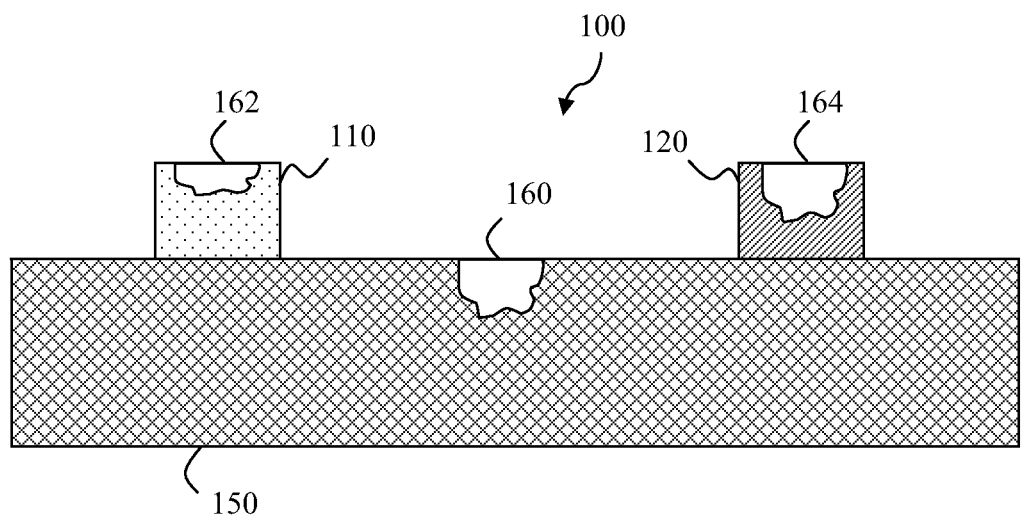
FIG. 3 depicts the sensor of FIG. 1 after the substrate has experienced erosion and corrosion.

Referring to FIG. 3, substrate 150 has suffered from corrosion and erosion, resulting in the formation of erosion/corrosion pit 160 on substrate 150. Sensor 100 can be used to provide an indication of erosion and/or corrosion on substrate 150. As shown, first element has an erosion pit 162 as a result of erosive substances acting on substrate 150. Erosion pit 162 has modified first conductive element 110 by reducing the cross-sectional area of first conductive element 110. This can be detected by an electrical property monitoring device, such as voltage or current meter, to provide an indication of erosion of the substrate 150. The change in resistance of the first conductive element 110 as a result of the formation of erosion pit 162 can be correlated to the amount or depth of erosion on the substrate 150.

As illustrated, the erosion pit 162 formed on first conductive element 110 is smaller than the erosion/corrosion pit 160 formed on substrate 150. This is because the first conductive element 110 is formed from a corrosion resistant material that does not exhibit the corrosion characteristics of the substrate 150 or second conductive element 120. As a result, the reduction in cross-section area of first conductive element 110 is based solely on erosion and provides a measure of erosion of substrate 150, exclusive of any corrosion occurring on substrate 150.

The erosion/corrosion pit formed on second conductive element 120 is similar in size and depth to the erosion/corrosion pit formed on substrate 150. This is because second conductive element 120 has similar erosion and corrosion properties to the substrate 150. The sensor 100 can provide a corrosion indicator based at least in part on the erosion and corrosion of the second element 120.

For instance, erosion/corrosion pit 164 has modified second conductive element 120 by reducing the cross-sectional area of the second conductive element 120. This can be detected by an electrical property monitoring device, such as voltage or current meter, to provide an indication of erosion and corrosion of the second conductive element 120. The change in resistance of the second conductive element 120 as a result of the formation of erosion/corrosion pit 164 can be correlated to the amount or depth of erosion/corrosion on the substrate 150. The amount of erosion/corrosion on the substrate 150 can be compared to the amount of erosion detected on the first conductive element 110 to specifically determine the amount of corrosion occurring on the substrate.

Figure 4:
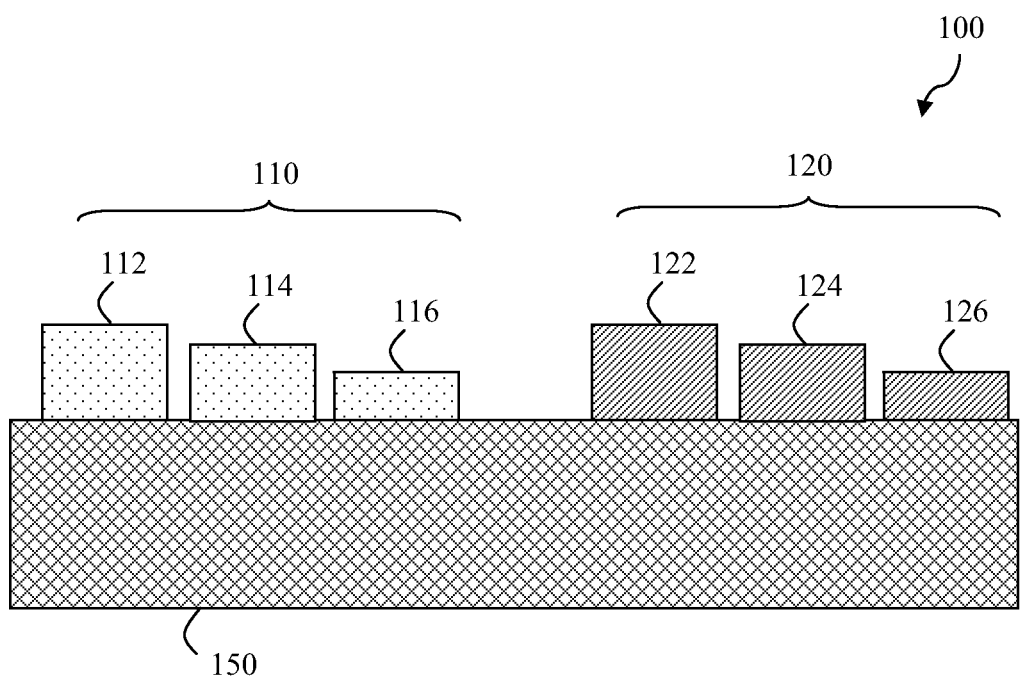
FIG. 4 depicts a sensor for monitoring erosion and corrosion disposed on a substrate according to another exemplary embodiment of the present disclosure.
Figure 5:
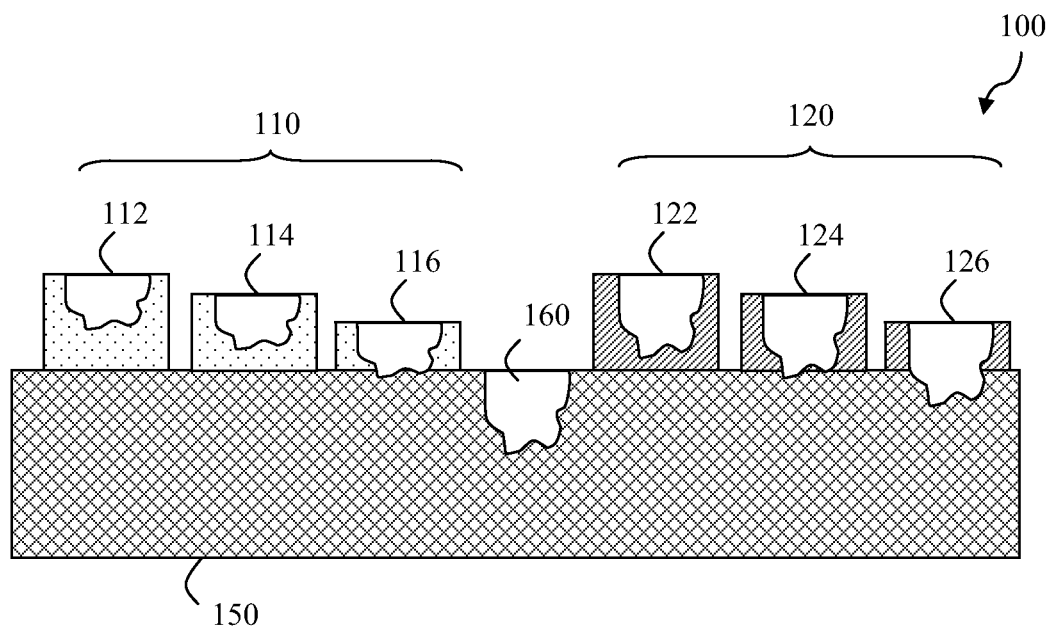
FIG. 5 depicts the sensor of FIG. 4 after the substrate has experienced erosion and corrosion.

Referring now to FIGS. 4-5 another exemplary sensor 100 according to an embodiment of the present disclosure will be discussed. Sensor 100 includes a plurality of first conductive elements 110 and a plurality of second conductive elements 120. Each of the first conductive elements 110 and each of the second conductive elements have a different thickness. Similar to the sensor depicted in FIGS. 2 and 3, the first conducting elements 110 shown in FIGS. 4 and 5 comprise a corrosion resistant material having similar erosion properties to the substrate 150. The second conducting elements 120 comprise a material having similar erosion and corrosion properties to the substrate 150.

The sensor 100 can be used to determine the depth of erosion and/or corrosion on the substrate 150. FIG. 5 shows a substrate 150 that has suffered from a degree of erosion and corrosion as illustrated by erosion/corrosion pit 160. The depth of erosion/corrosion pit 160 can be determined by sensor 100. In addition, the sensor 100 can determine how much of erosion/corrosion pit 160 is attributable to erosion and how much is attributable to corrosion.

More particularly, first conductive elements 110 include elements 112, 114, and 116. Substrate 150 has experienced erosion sufficient to sever or eat completely through element 116. This can be detected by an electrical parameter monitoring device which can provide a signal that element 116 has been completely severed. The erosion is not sufficient to completely sever or eat through elements 112 and 114. In this regard, sensor 100 provides an erosion indicator that the substrate 150 has been eroded to a depth at least as thick as the thickness of element 116, but not to a depth as thick as the thickness of elements 112 and 114.

Second conductive elements 120 include elements 122, 124, and 126. Substrate 150 has experienced erosion and corrosion sufficient to sever or eat completely through elements 124 and 26. This can be detected by an electrical parameter monitoring device which can provide a signal that elements 124 and 126 have been completely severed. The sensor 100 thus provides an indication that the substrate 150 has been eroded and corroded to a depth at least as thick as the thickness of elements 124 and 126, but not to a depth as thick as the thickness of element 122. This depth can be compared to the depth associated with erosion of the first elements 110 to provide a corrosion indicator of the depth of corrosion associated with the substrate 150.

Figure 6:
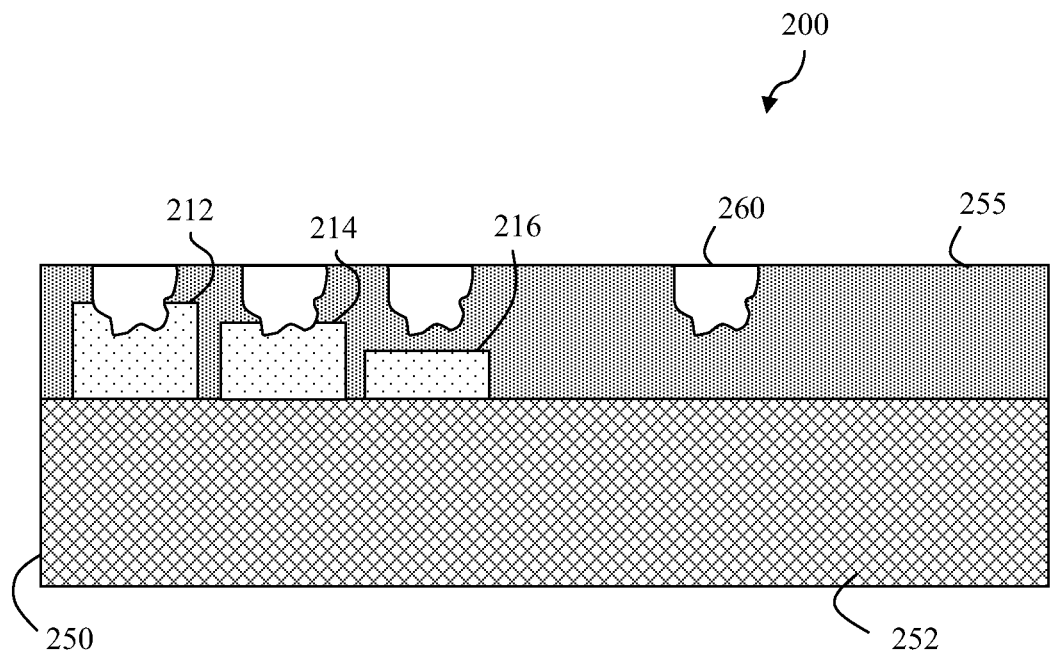
FIG. 6 depicts an erosion sensor for monitoring erosion of a coating applied to a substrate according to an exemplary embodiment of the present disclosure.

FIG. 6 depicts an exemplary sensor 200 that can be used to detect erosion of a coating 255 applied to a base layer 252 of a substrate 250 according to another exemplary embodiment of the present disclosure. Wind turbine blades and turbine blades used in devices such as gas turbines, aircraft engines, microturbines, steam turbines, and the like, can include a protective coating. In particular implementations, the coating can be intended to limit corrosion of the turbine blade. The coating, however, is still subject to erosion. It is desirable to monitor the amount of erosion occurring on the protective coating to ensure, for instance, that the turbine blade is not eroded to a depth that affects the turbine blade itself.

As shown in FIG. 6, erosion sensor 200 includes a plurality of conductive elements 212, 214, and 216 disposed within the coating 255. Conductive elements 212, 214, and 216 comprise a corrosion resistant material that has similar erosion properties to the coating 255 of the substrate. The conductive elements 212, 214, and 216 each have a different thickness such that the sensor 200 can provide an erosion indicator associated with the depth of erosion on the coating 255.

For instance, in a particular embodiment, sensor 200 can provide a first alert when coating 255 has been eroded to a depth sufficient to modify conductive element 212. Sensor 200 can provide a second alert when coating 255 has been eroded to a depth sufficient to modify conductive element 214. Finally, sensor 200 can provide a third alert when coating 255 has been eroded to a depth sufficient to modify conductive element 216.

By way of example, coating 255 of FIG. 6 has suffered from a degree of erosion as illustrated by erosion pit 260. The coating 255 has been eroded to a depth such that conductive elements 212 and 214 have been modified by reducing the cross-sectional area of the conductive elements 212 and 214. The sensor 200 provides an indication that coating 255 has suffered erosion to a depth sufficient to modify the second conductive element 214 and can provide an alert or other indication of the depth of erosion of the coating 255.

Figure 7:
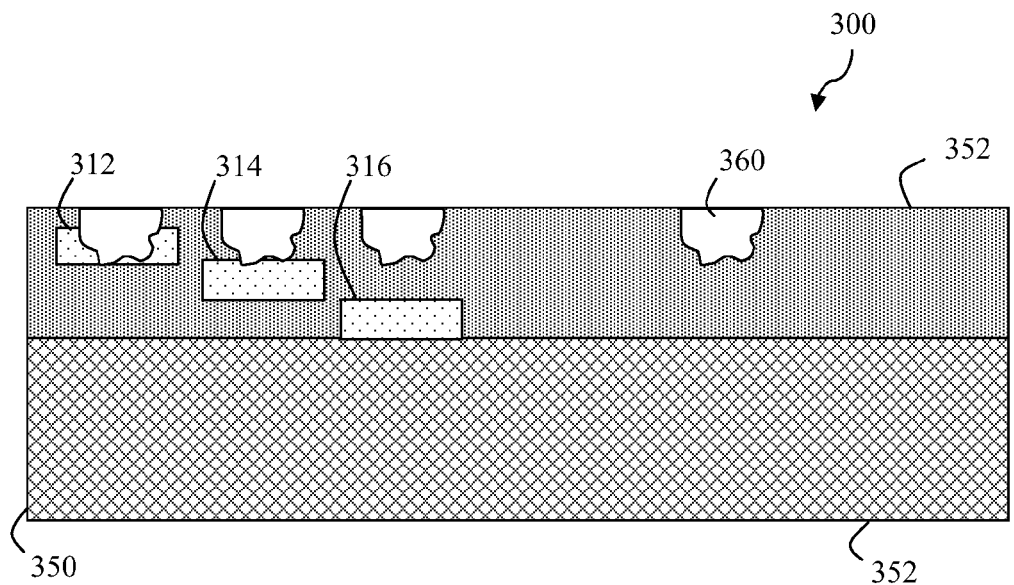
FIG. 7 depicts an erosion sensor for monitoring erosion of a coating applied to a substrate according to another exemplary embodiment of the present disclosure.

FIG. 7 depicts an exemplary sensor 300 that can be used to detect erosion of a coating 355 applied to a base layer 352 of a substrate 350 according to yet another exemplary embodiment of the present disclosure. Erosion sensor 300 includes a plurality of conductive elements 312, 314, and 316 disposed at different depths within the coating 355. Conductive elements 212, 214, and 216 comprise a corrosion resistant material that has similar erosion properties to the coating 355 of the substrate. The conductive elements 312, 314, and 316 are disposed at different depths within the substrate so that sensor 300 can provide an erosion indicator associated with the depth of erosion of the coating 355.

For instance, in a particular embodiment, sensor 300 can provide a first alert when coating 355 has been eroded to a depth sufficient to modify, sever or eat through conductive element 312. Sensor 300 can provide a second alert when coating 355 has been eroded to a depth sufficient to modify, sever or eat through conductive element 314. Finally, sensor 300 can provide a third alert when coating 355 has been eroded to a depth sufficient to modify, sever, or eat through conductive element 316.

By way of example, coating 355 of FIG. 7 has suffered from a degree of erosion as illustrated by erosion pit 360. The coating 355 has been eroded to a depth sufficient to sever conductive element 312, but not to sever or completely eat through conductive elements 314 or 316. The sensor 300 thus provides an indication that coating 355 has suffered erosion to a depth sufficient to sever conductive element 312 and can provide an alert or other indication of the depth of erosion of the coating 355.

Figure 8:
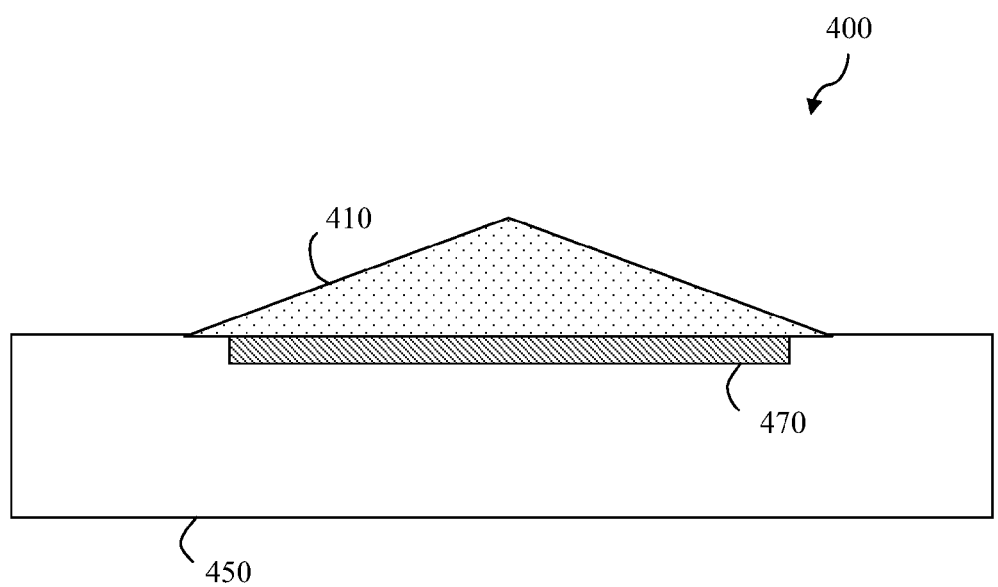
FIG. 8 depicts an erosion sensor disposed on a substrate according to yet another exemplary embodiment of the present disclosure.
Figure 9:
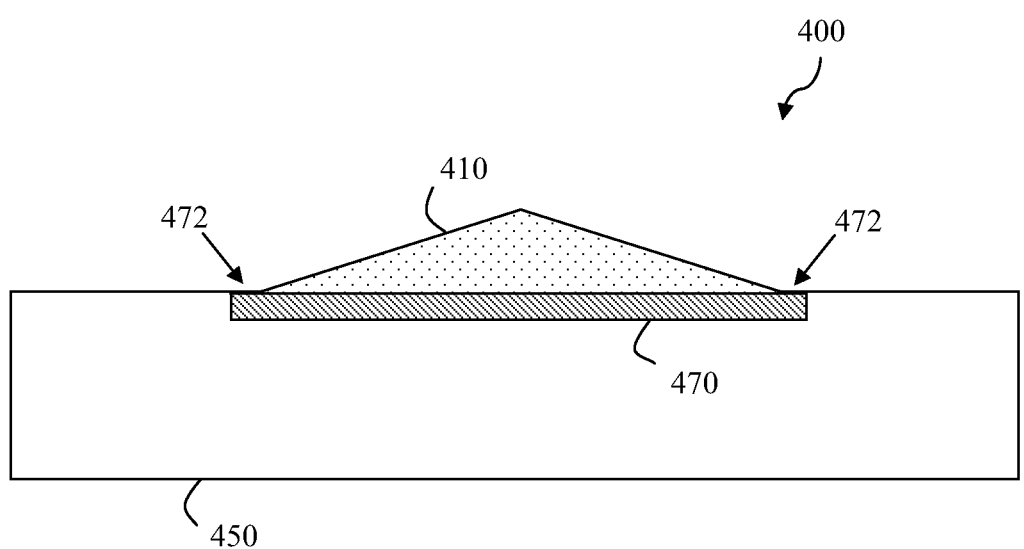
FIG. 9 depicts the erosion sensor of FIG. 8 after the erosion sensor has experienced erosion.

FIGS. 8-9 depict an exemplary sensor 400 according to another exemplary embodiment of the present disclosure. Sensor 400 is configured to provide an erosion indicator associated with the erosion of substrate 450, such as wind turbine blade. Sensor 400 includes a first element 410 of corrosion resistant material having similar erosion properties to the substrate 450. First element 410 has a tapered cross-section and is disposed on the substrate 450 so as to completely cover a colored portion 470 of the substrate 450.

As shown in FIG. 9, as the substrate 450 suffers from erosion, the tapered first element 410 has been sufficiently eroded to at least partially expose the colored portion 470 of substrate 450. This provides a visual erosion indicator 472, comprising the exposed color portion of the substrate 450, associated with the amount of erosion of the substrate 450. In this manner, the sensor 400 can provide a visual alert that can be viewed from a distance indicating that the substrate 450 has suffered a threshold amount of erosion.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A sensor for monitoring erosion and corrosion of a substrate, comprising:
   a first element of corrosion resistant material having similar erosion properties to the substrate; and
   a second element of material having similar erosion and corrosion properties to the substrate;
   wherein said sensor provides an erosion indicator based at least in part on erosion of said first element and provides a corrosion indicator based at least in part on erosion and corrosion of said second element, said corrosion indicator based on a comparison of the erosion of said first element and the erosion and corrosion of said second element, wherein said first element and said second element are planar and are disposed on a surface of the substrate.

2. The sensor of claim 1, wherein the first element comprises a conductive material, the erosion indicator comprising an electrical property associated with the first element.

3. The sensor of claim 2, wherein the electrical property comprises at least one of a voltage or a current across the first conductive element.

4. The sensor of claim 1, wherein the erosion indicator comprises an exposed color on a surface of the substrate.

5. The sensor of claim 4, wherein the first element has a tapered cross-section.

6. The sensor of claim 1, wherein the sensor comprises a plurality of first elements, each of said first elements having a different thickness, wherein said erosion of said plurality of first elements provides an indicator of erosion depth of the substrate.

7. The sensor of claim 1, wherein said first element comprises a metallic foil material, a fiber optic wire material, or a conductive polymer material.

8. The sensor of claim 1, wherein the substrate comprises a coating applied to a base layer, said first element being disposed within the coating of the substrate.

9. The sensor of claim 8, wherein the erosion of said first element provides an indication of erosion of the coating of the substrate.

10. The sensor of claim 1, wherein the first element and the second element are formed from different materials.

11. A system for monitoring erosion of a coating on a turbine blade, comprising:
    a plurality of conductive sensors disposed in the coating of the turbine blade, the conductive elements comprising a first element of corrosion resistant material having similar erosion properties to the coating of the turbine blade and a second element of a corroding material having similar erosion and corrosion properties to the coating of the turbine blade; and
    an electrical property monitoring device configured to monitor an electrical property associated with each of said plurality of conductive elements, said electrical property monitoring device providing a signal when one of said plurality of conductive elements has been modified due to erosion;
    wherein the system provides an erosion depth indicator based at least in part on the number of said plurality of conductive elements that have been modified due to erosion.

12. The system of claim 11, wherein said plurality of conductive elements each have a different thickness and are disposed on a surface of the turbine blade.

13. The system of claim 11, wherein said turbine blade comprises a coating, said plurality of first conductive elements being disposed at different depths within the coating of the turbine blade.

* * * * *